(12) United States Patent
Snyder

(10) Patent No.: US 9,593,357 B2
(45) Date of Patent: Mar. 14, 2017

(54) PROCESS TO CONTROL CO CONCENTRATIONS IN FERMENTATIONS

(71) Applicant: INEOS BIO SA, Rolle (CH)

(72) Inventor: David Scott Snyder, Fayetteville, AR (US)

(73) Assignee: INEOS BIO SA, Rolle (CH)

( * ) Notice: Subject to any disclaimer, the term of this patent is extended or adjusted under 35 U.S.C. 154(b) by 0 days.

(21) Appl. No.: 14/612,528

(22) Filed: Feb. 3, 2015

(65) Prior Publication Data

US 2015/0152464 A1 Jun. 4, 2015

Related U.S. Application Data

(62) Division of application No. 14/018,608, filed on Sep. 5, 2013, now Pat. No. 8,975,013.

(60) Provisional application No. 61/702,824, filed on Sep. 19, 2012, provisional application No. 61/702,826, filed on Sep. 19, 2012, provisional application No. 61/702,832, filed on Sep. 19, 2012, provisional application No. 61/702,837, filed on Sep. 19, 2012.

(51) Int. Cl.
| | |
|---|---|
| *G01N 33/84* | (2006.01) |
| *C12Q 1/04* | (2006.01) |
| *C12Q 3/00* | (2006.01) |
| *C12P 7/06* | (2006.01) |
| *C12P 7/08* | (2006.01) |
| *G01N 21/31* | (2006.01) |

(52) U.S. Cl.
CPC ............ *C12Q 1/04* (2013.01); *C12P 7/065* (2013.01); *C12P 7/08* (2013.01); *C12Q 3/00* (2013.01); *G01N 21/31* (2013.01); *G01N 33/84* (2013.01); *Y02E 50/17* (2013.01)

(58) Field of Classification Search
CPC ...................................................... G01N 33/84
See application file for complete search history.

(56) References Cited

U.S. PATENT DOCUMENTS

2010/0317077 A1* 12/2010 Gaddy ................ C12P 7/04
435/161

OTHER PUBLICATIONS

Riggs et al., "Measuring carbon monoxide gas-liquid mass transfer in a stirred tank reactor for syngas fermentation," Biotechnol Prog 22:903-906, 2006.*
Kundu et al., "Direct measurement of equilibrium constants for high-affinity hemoglobins," Biophysical Journal 84: 3931-3940, 2003.*

* cited by examiner

*Primary Examiner* — Rosanne Kosson
(74) *Attorney, Agent, or Firm* — James P. Krueger

(57) ABSTRACT

A process for controlling concentration of CO in a bioreactor provides a direct and real time measurement of dissolved CO in a fermentation medium. The process for controlling concentrations of CO in a bioreactor includes contacting an aliquot of fermentation medium with at least one CO binding ligand and at least one microbial inactivator.

7 Claims, 7 Drawing Sheets

PROCESS TO CONTROL CO CONCENTRATIONS IN FERMENTATIONS

This application is a divisional application of U.S. application Ser. No. 14/018,608, filed on Sep. 5, 2013. This application also claims the benefit of U.S. Provisional Application Nos. 61/702,824, 61/702,826, 61/702,832 and 61/702,837, all filed on Sep. 19, 2012, all of which are incorporated in their entirety herein by reference.

A process provides for control of concentrations of CO in a bioreactor that includes an aqueous fermentation medium. More specifically, the process includes contacting an aliquot of fermentation medium with at least one CO binding ligand and at least one microbial inactivator, and then measuring an amount of CO bound to the CO binding ligand.

BACKGROUND

Acetogenic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

Acetogenic microorganisms may be grown to produce ethanol from syngas that includes carbon monoxide. The growth process may involve culturing the acetogenic bacteria on increasing amounts of CO over time. High or low levels of CO in the fermentation may result in lower productivity.

Monitoring and control of fermentation condition are important for improving productivity during fermentation of gaseous substrates. Dissolved CO in a fermentation medium is typically a calculated number determined by using Henry's Law. Direct and real time measurement of dissolved CO concentrations in a fermentation medium would be effective for enhancing monitoring and control of the fermentation and enhancing productivity levels.

SUMMARY

A process for controlling concentration of CO in a bioreactor provides a direct and real time measurement of dissolved CO in a fermentation medium. The process may be used directly with a fermentation medium and can quickly determine CO concentrations. Direct and real time measurements of CO concentration allow for a more precise control of CO concentrations in the fermentation medium during syngas fermentations. Precise control of CO concentration is effective for enhancing productivity and preventing bioreactor failure.

A process for controlling concentrations of CO in a bioreactor that includes an aqueous fermentation medium includes contacting an aliquot of fermentation medium with at least one CO binding ligand and at least one microbial inactivator. In this aspect, aqueous fermentation medium includes microbes effective for consuming and/or producing CO. The process further includes measuring an amount of CO bound to the CO binding ligand. If the amount of CO bound to the CO binding ligand corresponds to a concentration of CO in the fermentation medium of about 10 µM or more, then a feed rate of CO to the bioreactor is decreased. Conversely, if the amount of CO bound to the CO binding ligand corresponds to a concentration of CO in the fermentation medium of about 2 µM or less, then a feed rate of CO to the bioreactor is increased.

In one aspect, the CO binding ligand includes a chelating agent or may include a nitrogen containing chelating agent. In another aspect, the CO bonding ligand is selected from the group consisting of hemoglobin, myoglobin, free heme, heme containing compounds, and mixtures thereof. The microbial inactivator is selected from the group consisting of salt, acid, base, organic solvent, oxidizing agents, heat, cold, and mixtures thereof. Absorbance measurements provide an indication of amount of CO bound to the CO binding ligand. In one aspect, the amount of CO bound to the CO binding ligand is a continuous measurement.

In another aspect, a process for measuring concentrations of CO in an aqueous fermentation medium includes contacting an aliquot of the fermentation medium with at least one CO binding ligand and at least one microbial inactivator. In this aspect, aqueous fermentation medium includes microbes effective for consuming and/or producing CO. The process further includes measuring an amount of CO bound to the CO binding ligand. In another aspect, the CO bonding ligand is selected from the group consisting of hemoglobin, myoglobin, free heme, heme containing compounds, and mixtures thereof. The microbial inactivator is selected from the group consisting of salt, acid, base, organic solvent, oxidizing agents, heat, cold, and mixtures thereof. Measurements may be made with or without cells present. Absorbance measurements provide an indication of amount of CO bound to the CO binding ligand. In one aspect, the amount of CO bound to the CO binding ligand is a continuous measurement.

In another aspect, a syngas fermentation process includes providing syngas to a bioreactor and fermenting the syngas. A dissolved CO concentration in a fermentation medium is controlled during the fermentation process by contacting an aliquot of fermentation medium with at least one CO binding ligand and at least one microbial inactivator, and measuring an amount of CO bound to the CO binding ligand. If the amount of CO bound to the CO binding ligand corresponds to a concentration of CO in the fermentation medium of about 10 µM or more, then a feed rate of CO to the bioreactor is decreased. If the amount of CO bound to the CO binding ligand corresponds to a concentration of CO in the fermentation medium of about 2 µM or less, then a feed rate of CO to the bioreactor is increased. The process effective for providing a total alcohol STY of about 1 g or more total alcohol/(L·day).

BRIEF DESCRIPTION OF FIGURES

The above and other aspects, features and advantages of several aspects of the process will be more apparent from the following figures.

Figure 1:
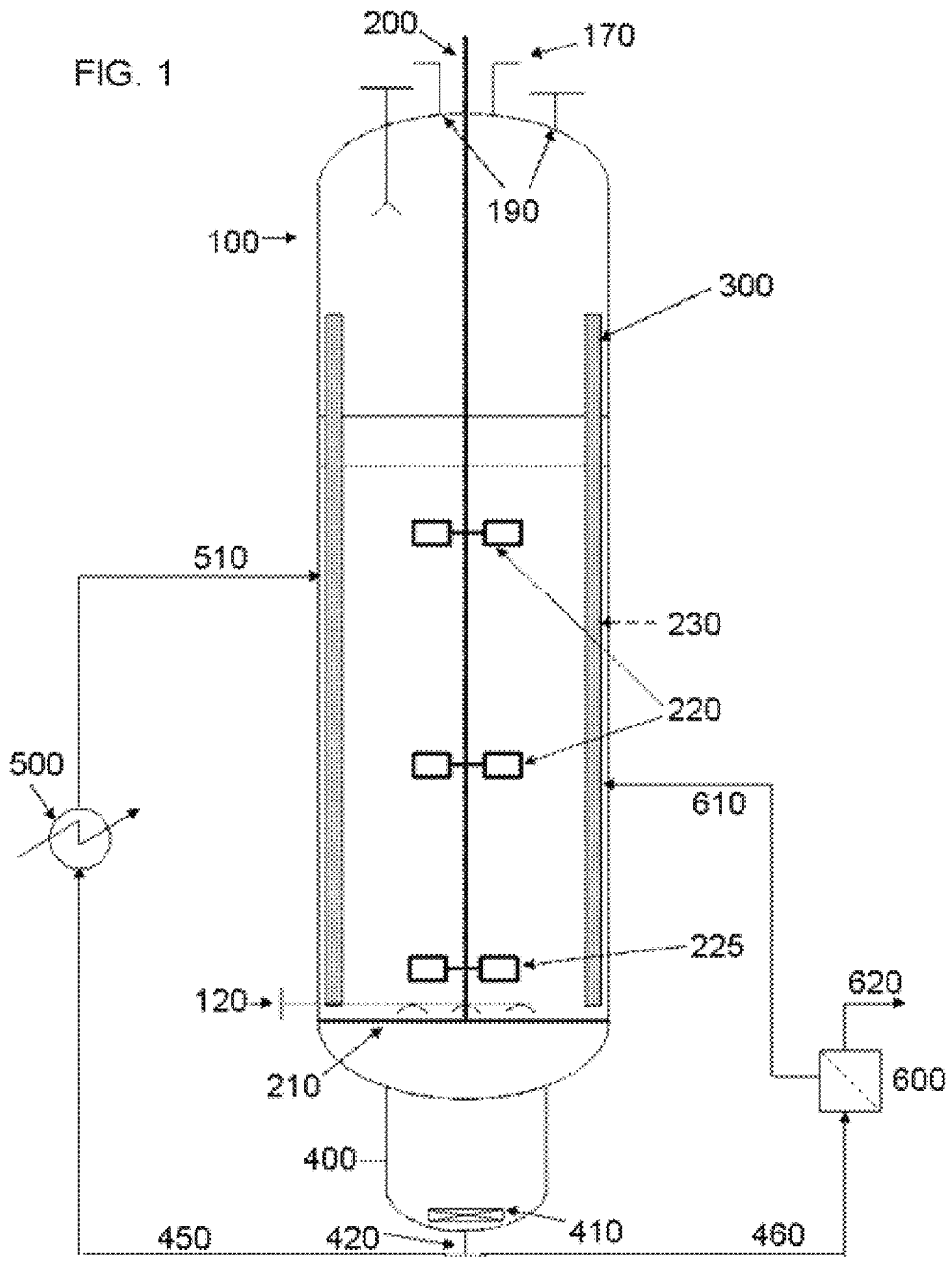
FIG. 1 is a perspective view of a bioreactor.

Corresponding reference characters indicate corresponding components throughout the several views of the figures. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

Syngas fermentations conducted in bioreactors with medium and acetogenic bacteria as described herein are effective for providing conversions of CO in syngas into alcohols and other products. Control of CO concentrations in the fermentation through measurement of dissolved CO in the fermentation medium is effective for providing high productivity levels. In this aspect, productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

DEFINITIONS

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation medium, for example, grams/liter.

The term "cell recycle" refers to separation of microbial cells from a fermentation medium and returning all or part of those separated microbial cells back to the fermentor. Generally, a filtration device is used to accomplish separations.

The term "increasing the efficiency", "increased efficiency" and the like, when used in relation to a fermentation process includes increasing one or more of the rate of growth of microorganisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of fermentation.

Bioreactor Design

Any known bioreactors may be utilized. Some examples of bioreactors are described in U.S. Ser. Nos. 61/571,654 and 61/571,565, filed Jun. 30, 2011, U.S. Ser. No. 61/573, 845, filed Sep. 13, 2011, U.S. Ser. Nos. 13/471,827 and 13/471,858, filed May 15, 2012, and U.S. Ser. No. 13/473, 167, filed May 16, 2012, all of which are incorporated herein by reference.

FIG. 1 is a perspective view of one example of a bioreactor apparatus. The bioreactor apparatus includes a housing defining a reactor vessel 100. The reactor vessel 100 may be substantially cylindrical and a cross section of the reactor vessel may be shaped in the form of a circle, substantially circular, or other shapes that are effective for improving mixing and mass transfer.

As further shown in FIG. 1, syngas enters the reactor vessel 100 through a gas inlet/distributor/sparger 120. Dispersion of the syngas and further mixing is accomplished with at least one gas dispersion impeller 225 and at least one mixing impeller 220 which are coupled to a drive shaft 200. The drive shaft 200 is supported by an agitator support plate 210. Gas is exhausted from the reactor vessel 100 through exhaust valve 170. The reactor may include other addition or removal ports such as illustrated by 190. The reactor vessel 100 may also include baffles 300 to further enhance mixing.

In another aspect, the reactor vessel 100 may include addition ports 230. The addition ports 230 may include for example, one or more acidic addition ports, one or more alkaline addition ports, and one or more nutrient addition ports. In this aspect, the addition ports may be equally spaced apart around a circumference of the reaction vessel. The ports may be on the same or different horizontal plane.

Addition ports may be modified to allow for removal of aliquots of fermentation medium.

As further illustrated in FIG. 1, the reactor vessel 100 may also include a boot 400 and a vortex breaker 410 disposed within the boot and over a medium outlet 420. The boot 400 and vortex breaker 410 are effective for preventing gas from being drawn out through the medium outlet 420. Medium drawn out through medium outlet 420 may be sent to a medium to recycle loop 450 or to a medium filter loop 460. Medium from the medium recycle loop 450 may be sent to a cooler/heat exchanger 500 and cooled medium 510 may be cycled back to the reactor vessel 100.

Medium from the medium filter loop 460 may be sent to a recycle filter 600. Concentrated cells 610 are returned to the reactor vessel 100 and permeate 620 is sent for further processing. Further processing may include separation of desired product such as for example ethanol, acetic acid and butanol.

Aliquots of fermentation medium for CO analysis may be removed from medium outlet 420, recycle loop 450, medium filter loop 460, and/or permeate 620. In another aspect, aliquots of fermentation medium may be drawn directly from the reactor vessel 100 through a sample port (not shown).

Figure 2:
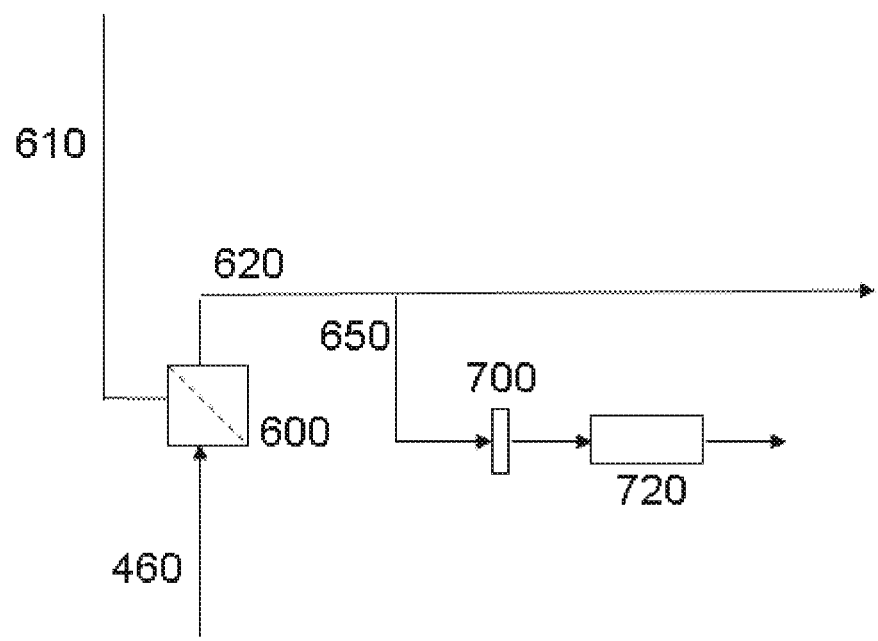
FIG. 2 illustrates a system for continuous measurement of CO after removal of cells.

In another aspect shown in FIG. 2, permeate 620 from the recycle filter 600 may be utilized for measurement of CO concentration. In this aspect, a permeate side stream 650 may be removed from the permeate 620. CO binding ligand and microbial inactivator may be added at reagent addition port 700. An amount of CO bound to the CO binding ligand may be measured in a detector 720. In this aspect, the detector 720 may be a flow through cell. A flow rate of the permeate side stream 650 may be controlled to provide an effective amount of time for CO to bind to the CO binding ligand. Flow through cells and absorbance measurements may be done using known equipment and procedures.

Figure 3:
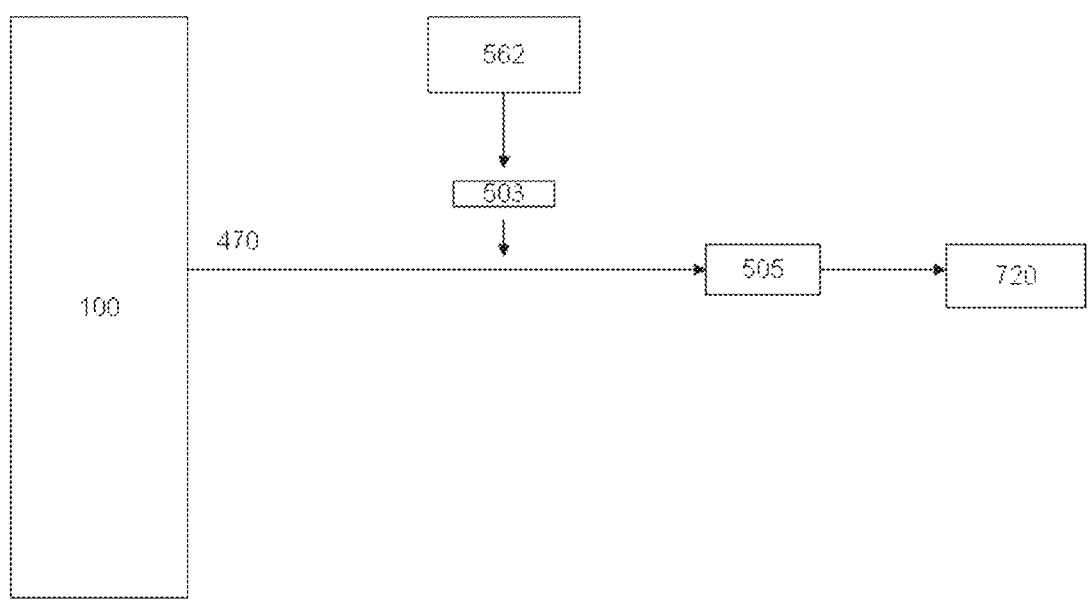
FIG. 3 shows a system for measurement of CO with cells present.

In another aspect shown in FIG. 3, cells and fermentate 470 are withdrawn from the fermentor 100. A reservoir pump 503 is effective for contacting a hemoglobin and salt solution from a hemoglobin salt solution reservoir 562 with the cells and fermentate 470. A pump 505 may effect transfer to a detector 720. Pump flow rates may be controlled to provide an effective amount of time for CO to bind to the CO binding ligand. An amount of CO bound to the CO binding ligand may be measured in a detector 720. In this aspect, the detector 720 may be a flow through cell. Flow through cells and absorbance measurements may be done using known equipment and procedures.

Figure 4:
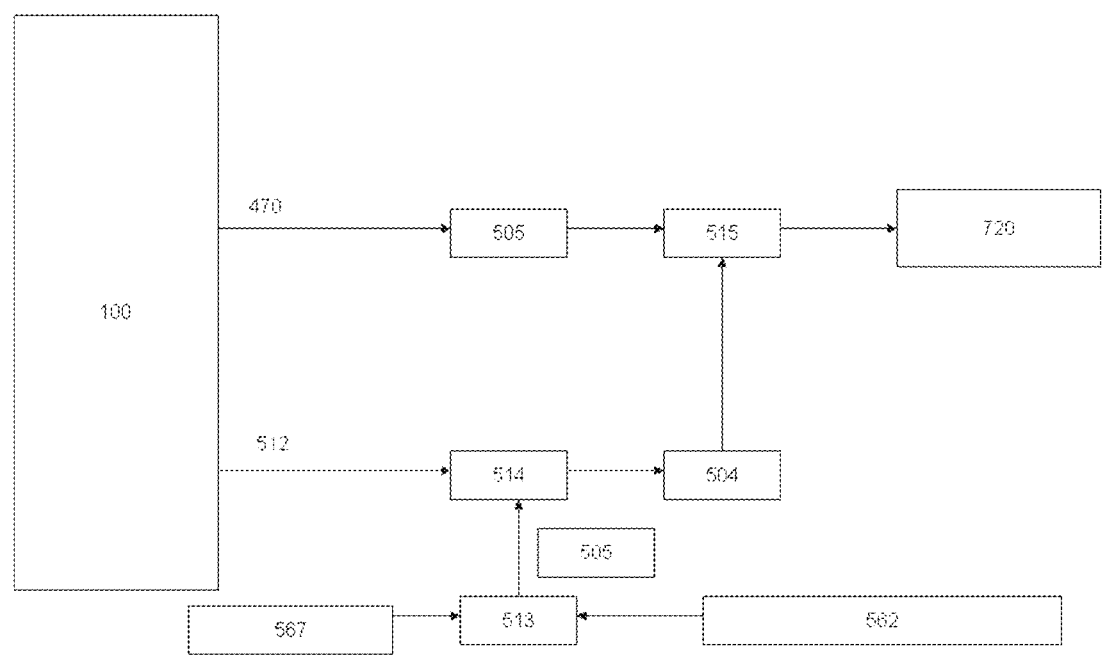
FIG. 4 shows a multipurpose analytical port design.

A multipurpose analytical port design is illustrated in FIG. 4. In one aspect, a pump 505 may effect removal of fermentate and cells 470 from a fermentor 100. The fermentate and cells 470 may be conveyed to a three way valve 515 which is effective for controlling blending of the fermentate and cells 470 with an appropriate reagent and effecting transfer to a detector 720.

In another aspect shown in FIG. 4, the fermentor 100 may include a sampling probe 512. Aqueous sample provided by the sampling probe 512 may be conveyed to a sample probe three way valve 514 which may effect contact with an appropriate reagent. A reservoir pump 503 may be utilized to provide reagent from a reagent reservoir 567 and/or hemoglobin salt solution from a hemoglobin salt reservoir 562 to the reservoir three way value 513 and to the sample probe three way valve 514. A sample pump 504 may be utilized to provide sample contacted with an appropriate reagent and/or hemoglobin salt solution to three way vale 515.

In one aspect, the sampling probe 512 may be any type of sampling probe known in the art. One example of an appropriate sampling probe is an FISP® probe (available from Flownamics). The FISP® probe is a sampling probe capable of withdrawing sterile, cell-free samples from the fermentor. FISP® allows direct on-line sample transfer to a variety of analyzers, such as biochemistry and HPLC systems, as well as collection for off-line analysis. FISP® is a small, tube-shaped, sterilizable 316 stainless steel carrier which is surrounded by a tubular, micro-porous membrane.

In another aspect, tubing utilized for sampling should be gas impermeable. In this aspect, tubing should be non-metallic and non-ferrous. On example of tubing that may be utilized includes tubing made from polyetheretherketone.

Medium

In accordance with one aspect, the fermentation process is started by addition of a suitable medium to the reactor vessel. The liquid contained in the reactor vessel may include any type of suitable nutrient medium or fermentation medium. The nutrient medium will include vitamins and minerals effective for permitting growth of the microorganism being used. Anaerobic medium suitable for the fermentation of ethanol using CO as a carbon source are known. One example of a suitable fermentation medium is described in U.S. Pat. No. 7,285,402, which is incorporated herein by reference. Other examples of suitable medium are described in U.S. Ser. Nos. 61/650,098 and 61/650,093, both filed on May 22, 2012, and which are both incorporated herein by reference.

Syngas

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The syngas will have a $CO/CO_2$ ratio of at least about 0.75. Some examples of suitable gasification methods and apparatus are provided in U.S. Ser. Nos. 13/427,144, 13/427,193 and 13/427,247, all of which were filed on Mar. 22, 2012, and all of which are incorporated herein by reference.

In another aspect, syngas utilized for propagating acetogenic bacteria may be substantially CO. As used herein, "substantially CO" means at least about 50 mole % CO, in another aspect, at least about 60 mole % CO, in another aspect, at least about 70 mole % CO, in another aspect, at least about 80 mole % CO, and in another aspect, at least about 90 mole % CO.

Acetogenic Culture

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593, 886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* 0-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

Determination of CO Concentrations

Sampling:

In one aspect, the process includes contacting an aliquot of fermentation medium with at least one CO binding ligand and at least one microbial activator. The process may include taking an aliquot of fermentation medium directly from the bioreactor or from various recycle loops associated with the bioreactor. The amount of fermentation medium removed corresponds to any amount effective for providing an accurate determination of CO concentration. In this aspect, the amount of fermentation medium removed is adjusted based on expected CO concentration levels. Generally, sample amounts will range from about 0.02 ml to about 20 ml, in another aspect about, 1 ml to about 7 ml, in another aspect, about 0.1 ml to about 1 ml, in another aspect about 5 ml to about 10 ml, and in another aspect about 7 ml to about 8 ml.

Aliquots removed from the bioreactor will include fermentation medium and microbes capable of producing and/or consuming CO. Fermentation mediums may include known mediums as described herein. Microbes capable of producing and/or consuming CO include acetogenic bacteria as described herein. In one aspect, the process may include removal of microbes from the aliquots of fermentation medium prior to CO measurements. In another aspect, the process may include analysis without removal of microbes.

CO Binding Ligand:

CO binding ligands are effective for bonding to dissolved CO in the fermentation medium. In another aspect, examples of CO binding ligands include hemoglobin, myoglobin, free heme, heme containing compounds, and mixtures thereof.

In an alternative aspect, the CO binding ligand includes a chelating agent. In this aspect, the chelating agent is a non-heme containing compound capable of binding CO.

Amounts of CO binding ligand utilized will be in an excess of the amount of CO that may be in the sample. Generally, the amount of CO binding ligand utilized in the process will be about 7 mg/ml or more.

Microbial Inactivator:

Microbial inactivators are effective for preventing any microbes in the sample from consuming or creating CO. In this aspect, microbial inactivators may include salt, acid, base, oxidizing agents, organic solvent, heat, cold, and mixtures thereof. In the aspect where the microbial inactivator is a salt, the salt may include NaCl, KCl, ammonium chloride, sodium sulfate, sodium bromide, and mixtures thereof. The salt solution will be at a concentration effective for inactivating microbes capable of consuming or creating CO. In this aspect, the salt solution will have a concentration of 0.2 to about 5 M.

In the aspect where the microbial inactivator is an acid or base, the acid may include HCl, sulfuric acid, trifluroacetic acid, acetic acid, and mixtures thereof, and the base may include NaOH, ammonium hydroxide, triethylamine, potassium hydroxide, and mixtures thereof. The acid or base solution will be at a concentration effective for inactivating microbes capable of consuming or creating CO. In this aspect, the acid solution will have a concentration of about 0.02 to about 5 M, and the base will have a concentration of about 0.02 to about 5 M. In this aspect, where the inactivator is hydrogen peroxide, the concentration may be from about 1% to about 3%. In the aspect where cold is used, temperatures from about −270° C. to about 0° C. are effective. In the aspect where heat is used, temperatures from about 35° C. to about 100° C. are effective.

Absorbance Measurement:

Any known spectrophotometric equipment may provide absorbance measurements. Some examples of spectrophotometric equipment include Beckman Coulter sectrophotometers (DU 800, DU730) and microplate readers such as the Spectramax (M1, M2, and M3). In this aspect, a ratio of absorbance measurements at 538 nm and 555 nm provides a measure of CO bound to CO binding ligand. In another aspect, the process may include use of a flow through cell in connection with an appropriate spectrophotometer to provide continuous absorbance measurements.

Bioreactor Operation

In accordance with one aspect, the fermentation process is started by addition of medium to the reactor vessel. The medium is sterilized to remove undesirable microorganisms and the reactor is inoculated with the desired microorganisms.

Upon inoculation, an initial feed gas supply rate is established effective for supplying the initial population of microorganisms. Concentrations of dissolved CO in the fermentation medium are determined as described herein. If the amount of CO bound to the CO binding ligand corresponds to a concentration of CO in the fermentation medium of 10 $\mu$M or more, then a feed rate of CO to the bioreactor is decreased. In another aspect, if the amount of CO bound to the CO binding ligand corresponds to a concentration of CO in the fermentation medium of 2 $\mu$M or less, then a feed rate of CO to the bioreactor is increased.

EXAMPLES

Example 1

Measurement of CO

Hemoglobin Solution was Prepared as Follows:

A 7 mg/ml solution of bovine hemoglobin was prepared in a 100 mM carbonate buffer (pH 9.3). Sodium dithionite (20 mg/ml) was added and the mixture was centrifuged at 7500 g at 4° C. Supernatant was removed and one half volume of 5 M NaCl was added.

Standards were Prepared as Follows:

A syngas sparged water solution (0.0, 0.01, 0.02, 0.05, 0.1, 0.2 and 0.3 ml) was added to a 0.6 ml of hemoglobin/salt solution in a 2 ml centrifuge tube. Water was added to bring total volumes to 2.0 ml.

Sampling was Conducted as Follows:

Hemoglobin/salt solution was drawn into a serological syringe equipped with a stopcock. Sampling of fermentate was conducted by drawing a sample from a cell recycle system from a "T" off a main line from a bioreactor that was fermenting syngas. Lines were first cleared by withdrawing about 10 ml of fermentate. A 7 ml aliquot of fermentate was then rapidly removed with the syringe containing the hemoglobin/salt solution pointing downward to effect mixing the fermentate with the hemoglobin/salt solution.

Absorbance Measurements were Conducted as Follows:

All samples and standards were held at room temperature for a minimum of 10 minutes and a maximum of 2 hours. Absorbance of standards and samples was determined at 538 nm and 555 nm.

Figure 5:
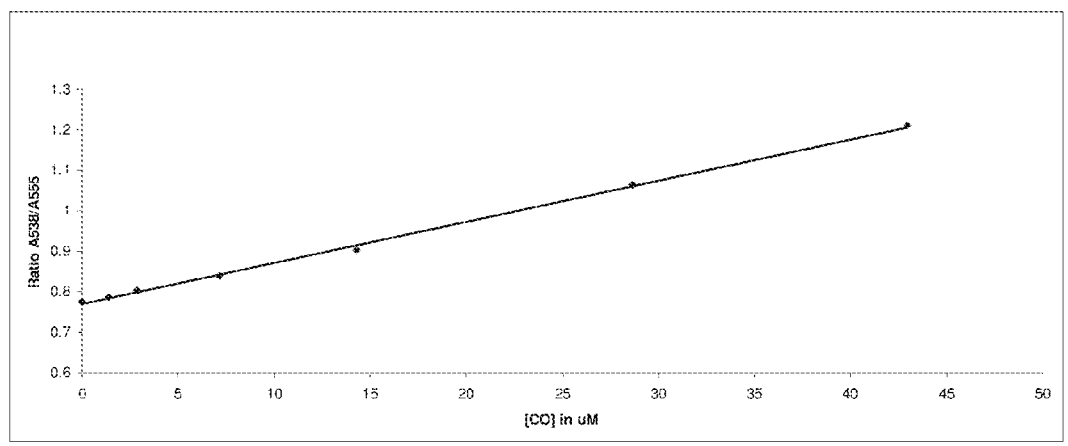
FIG. 5 illustrates a standard curve showing a ratio of absorbance at 538:555 nm versus CO concentration in µM.

Calculating CO Concentration:

Using a Henry's Law constant of 0.00095 M/atm, stock concentrations of CO were calculated based on a percentage of CO in the syngas. A standard curve showing a ratio of absorbance at 538:555 nm versus CO concentration in µM is shown in FIG. 5.

Example 2

Loss of CO

Figure 6:
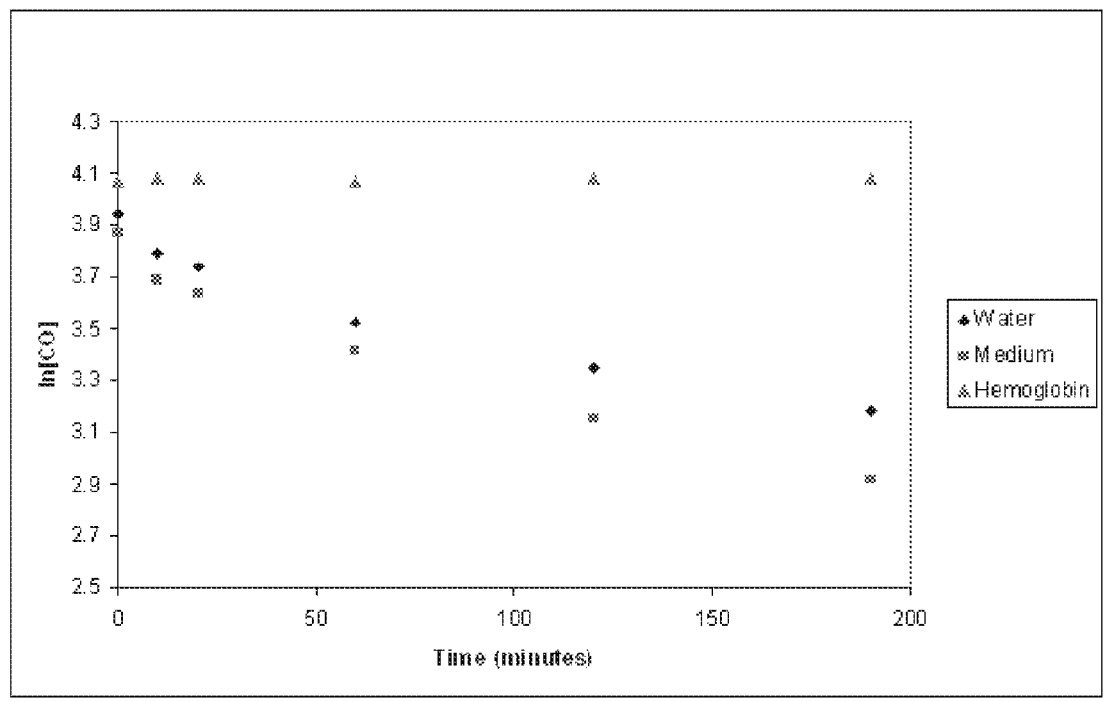
FIG. 6 illustrates loss of CO from water and medium over time and illustrates that hemoglobin prevents loss of CO from water.

Solutions of water and fermentation medium were sparged with CO. A hemoglobin solution was added to some aliquots of CO sparged water. Concentrations of CO were measured as described in Example 1. FIG. 6 illustrates loss of CO from water and medium over time and illustrates that hemoglobin prevents loss of CO from water.

Figure 7:
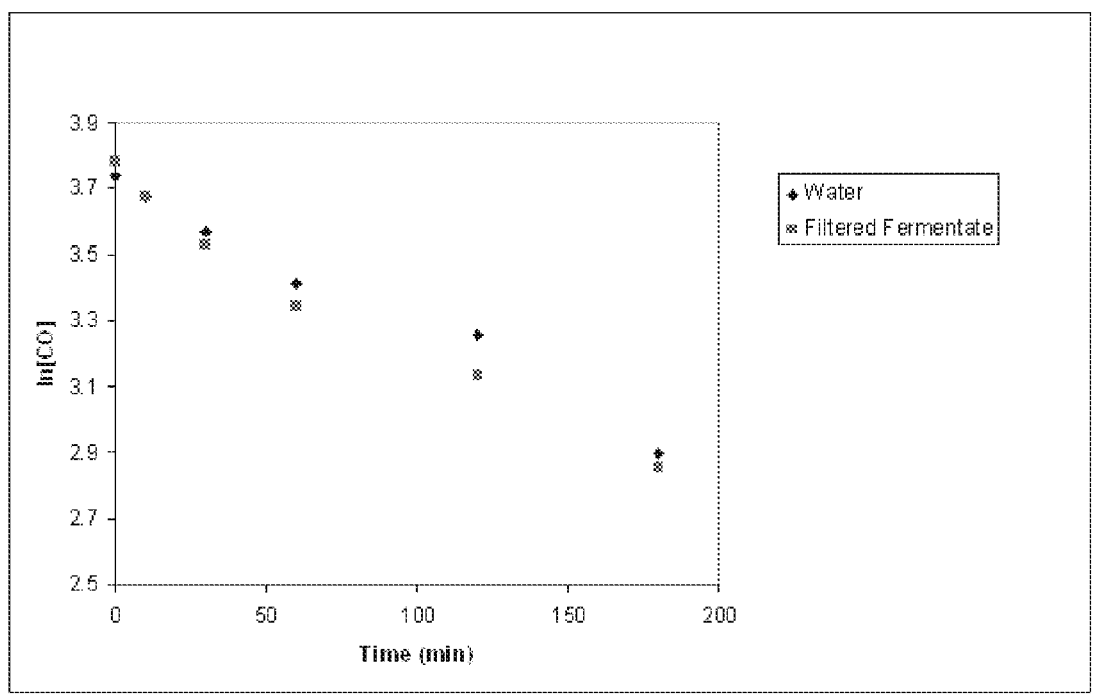
FIG. 7 illustrates loss of CO in filtered fermentate over time.

Concentrations of CO in samples of fermentate were measured with time. FIG. 7 illustrates loss of CO in filtered fermentate over time.

While the invention herein disclosed has been described by means of specific embodiments, examples and applications thereof, numerous modifications and variations could be made thereto by those skilled in the art without departing from the scope of the invention set forth in the claims.

What is claimed is:

1. A process for measuring a concentration of CO in an aqueous fermentation medium, the process comprising:
   i) contacting an aliquot of the fermentation medium that includes acetogenic bacteria with at least one CO binding ligand and at least one microbial inactivator selected from the group consisting of a salt, acid, base, organic solvent, oxidizing agent, heat, cold and mixtures thereof, wherein the sat is selected from the group consisting of sodium chloride, potassium chloride ammonium chloride sodium bromide and mixtures thereof; and
   ii) measuring an amount of CO bound to the CO binding ligand.

2. The process of claim 1 wherein the CO bonding ligand is selected from the group consisting of hemoglobin, myoglobin, free heme, heme containing compounds, and mixtures thereof.

3. The process of claim 1 wherein the amount of CO bound to the CO binding ligand is measured by determining changes in absorbance.

4. The process of claim 1 wherein the acetogenic bacterium is selected from the group consisting of *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsonii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Runtinococcus productus, Thermoanaerobacter kivui*, and mixtures thereof.

5. The process of claim 1 wherein the microbial inactivator is a salt solution having a concentration of about 0.2 to about 5M.

6. The process of claim 1 wherein the microbial inactivator is an acid solution having a concentration of about 0.02 to about 5M.

7. The process of claim 1 wherein the microbial inactivator is a base solution having a concentration of about 0.02 to about 5M.

* * * * *